(12) United States Patent
Neusigl et al.

(10) Patent No.: US 12,132,232 B2
(45) Date of Patent: Oct. 29, 2024

(54) BIPOLAR PLATE, RETENTION SAMPLE FOR A BIPOLAR PLATE, SYSTEM, AND METHOD FOR PRODUCING AND TESTING A BIPOLAR PLATE

(71) Applicant: Reinz-Dichtungs-GmbH, Neu-Ulm (DE)

(72) Inventors: Michaela Neusigl, Blaustein (DE); Kai-Uwe Lemke, Ulm (DE); Harald Liedtke, Thannhausen (DE); André Speidel, Bussmannshausen (DE); Bernhard Walter, Neu-Ulm (DE)

(73) Assignee: REINZ-DICHTUNGS-GMBH, Neu-Ulm (DE)

( * ) Notice: Subject to any disclaimer, the term of this patent is extended or adjusted under 35 U.S.C. 154(b) by 591 days.

(21) Appl. No.: 17/372,220

(22) Filed: Jul. 9, 2021

(65) Prior Publication Data
US 2022/0013794 A1   Jan. 13, 2022

(30) Foreign Application Priority Data
Jul. 10, 2020   (DE) ..................... 10 2020 208 693.1

(51) Int. Cl.
*H01M 8/0247* (2016.01)
*G01N 33/20* (2019.01)
*G01N 33/00* (2006.01)

(52) U.S. Cl.
CPC .......... *H01M 8/0247* (2013.01); *G01N 33/20* (2013.01); *G01N 33/0078* (2024.05)

(58) Field of Classification Search
None
See application file for complete search history.

(56) References Cited

U.S. PATENT DOCUMENTS

| | | | | |
|---|---|---|---|---|
| 2,328,253 A | * | 8/1943 | Becker | ............................ 40/203 |
| 7,749,636 B2 | * | 7/2010 | Scherer | ................. H01M 8/028 |
| | | | | 429/457 |
| 2016/0079615 A1 | * | 3/2016 | Scherer | ............... B32B 38/0004 |
| | | | | 429/413 |

FOREIGN PATENT DOCUMENTS

| | | | | | |
|---|---|---|---|---|---|
| CN | 100348464 C | * | 11/2007 | ......... | B65D 17/4014 |
| DE | 3627693 A | * | 2/1988 | ......... | B65D 73/0007 |
| DE | 102008005444 A1 | | 7/2009 | | |
| DE | 102018218487 A1 | | 4/2020 | | |
| GB | 2283271 A | * | 5/1995 | ............. | G08B 25/12 |
| GB | 2402704 A | * | 12/2004 | ......... | B65D 63/1063 |
| JP | 5409781 B | * | 2/2014 | ......... | B65D 17/4014 |

* cited by examiner

*Primary Examiner* — Daniel S Larkin
(74) *Attorney, Agent, or Firm* — McCoy Russell LLP (57) ABSTRACT

The present disclosure relates to a bipolar plate for an electrochemical system, comprising two separator plates which are connected to one another, at least one of the separator plates having a plate body and at least one tab which is formed in one piece with the plate body and can be separated from the plate body via a predetermined breaking point. The disclosure additionally relates to a retention sample for a bipolar plate or flow plate, to a flow plate, to a system, and to a method for producing and testing a bipolar plate or flow plate.

16 Claims, 8 Drawing Sheets

Fig. 9
(VIII-VIII)

BIPOLAR PLATE, RETENTION SAMPLE FOR A BIPOLAR PLATE, SYSTEM, AND METHOD FOR PRODUCING AND TESTING A BIPOLAR PLATE

CROSS-REFERENCE TO RELATED APPLICATION

The present application claims priority to German Patent Application No. 10 2020 208 693.1, entitled "BIPOLAR PLATE, RETENTION SAMPLE FOR A BIPOLAR PLATE, SYSTEM, AND METHOD FOR PRODUCING AND TESTING A BIPOLAR PLATE," and filed on Jul. 10, 2020. The entire contents of the above-listed application are hereby incorporated by reference for all purposes.

TECHINCAL FIELD

The present document relates to a bipolar plate for an electrochemical system, to a retention sample for a bipolar plate or flow plate, to a system comprising a retention sample and a bipolar plate or flow plate, to a flow plate, to a method for producing a bipolar plate or flow plate, and to a method for testing a retention sample of a bipolar plate or flow plate. The electrochemical system may be, for example, a fuel cell system, an electrochemical compressor, a redox flow battery, a humidifier for an electrochemical system, or an electrolyser.

BACKGROUND AND SUMMARY

Known electrochemical systems usually comprise a stack of electrochemical cells, which are each separated from one another by bipolar plates. Such bipolar plates may serve for example for indirectly electrically contacting the electrodes of the individual electrochemical cells (for example fuel cells) and/or for electrically connecting adjacent cells (series connection of the cells). The bipolar plates are typically formed of two individual plates which are joined together, which plates can also be referred to as separator plates. The separator plates of the bipolar plate may be joined together by a material bond, for example by one or more welded joints, for example by one or more laser-welded joints.

The bipolar plates and/or the separator plates may each have or form structures which are configured for example to supply one or more media to the electrochemical cells bounded by adjacent bipolar plates and/or to remove reaction products therefrom. The media may be fuels (for example hydrogen or methanol) or reaction gases (for example air or oxygen). Furthermore, the bipolar plates and/or the separator plates may have structures for guiding a cooling medium through the bipolar plate, for example through a cavity enclosed by the separator plates of the bipolar plate. Furthermore, the bipolar plates may be configured to transmit the waste heat that arises when converting electrical and/or chemical energy in the electrochemical cell, and also to seal off the various media channels and cooling channels with respect to one another and/or with respect to the outside.

Furthermore, the bipolar plates usually each have multiple through-openings. Through the through-openings, the media and/or the reaction products can be conducted to the electrochemical cells bounded by adjacent bipolar plates of the stack or into the cavity formed by the separator plates of the bipolar plate, or can be conducted out of the cells or out of the cavity. The electrochemical cells typically also each comprise one or more membrane electrode assemblies (MEAs). The MEAs may have one or more gas diffusion layers, which are usually oriented towards the bipolar plates and are configured for example as a metal or carbon fleece.

The separator plates, as well as the flow plates, may each be formed from a shaped metal sheet, for example from an embossed or deep-drawn stainless steel sheet. This metal sheet often has a thickness of approximately 60 μm to at most 150 μm. Since these are therefore very delicate, yet relatively large components, bipolar plates or separator plates may under certain circumstances be difficult to handle. On the one hand, the separator plates or bipolar plates may react sensitively to mechanical deformations due to the small thickness of the separator plates. In addition, contamination of areas that have yet to be coated or that have already been coated is to be avoided. However, due to the multifarious nature of their surface, which serves a range of functions, separator plates or bipolar plates should usually only be handled in the substantially unstructured edge region thereof. It has been found in practice that this is not always possible due to sharp edges, or that this is not always done. People or machines that have to deal with these separator plates or bipolar plates are therefore not always able to transport, position, grip or handle the separator or bipolar plates in the proper way. As a result, there is often either contamination of the separator plates or bipolar plates, for example caused by fingerprints of people or residues from suction lifting tools, for example of automatic gripper systems, and/or deformations of the separator plates or bipolar plates or inaccurate positioning of the separator plates or bipolar plates.

Another problem lies in the quality assurance of the separator plates, flow plates or bipolar plates, since customary measuring methods can be used on the finished component only to a limited extent or only in a destructive manner.

It would additionally be desirable if a traceability of the finished bipolar plate or flow plate can be created, for example in case of complaints.

The object of the present disclosure is to solve at least one or more of the problems mentioned above.

According to a first aspect, a bipolar plate for an electrochemical system is provided. The bipolar plate comprises two separator plates which are connected to one another, at least one of the separator plates having a plate body and at least one tab which is formed in one piece with the plate body and can be separated from the plate body via a predetermined breaking point.

The tab may perform one or more functions. The tab may simplify and/or enable the transporting, traceability and/or process monitoring of the bipolar plate. To this end, the tab may have functional elements designed for this. In the following description, various aspects of the tab and/or of these functional elements will be described in greater detail.

The tab is usually configured for transporting, positioning, holding and/or gripping the bipolar plate or the separator plate. As a result, the separator plate or bipolar plate can be handled at the tab, without the plate body being contaminated by fingerprints or by residues of a lifting tool, for example a suction lifting tool, for example of an automatic gripper system, or being mechanically deformed. The predetermined breaking point is often configured such that it does not break and does not plastically deform under the weight of the separator plate or bipolar plate. A deformation of the tab, on the other hand, is permitted, for example at the time of separation. The tab may have a holding area, which is intended to be held by humans or machines and can be dimensioned accordingly. The holding area may for example form a flat surface portion on the tab. For positioning the separator plate or bipolar plate, it may be advantageous that the tab has a positioning opening for receiving a centring pin. If the tab is used only for transporting, positioning, holding and/or gripping a separator plate and/or bipolar plate, the separation of the tab may take place at any suitable point in time during or at the end of the production process or else not until during or after the installation process.

The at least one tab may be provided at various suitable points of the bipolar plate. The tab or a tab plane often extends in or parallel to a plate plane defined by the plate body. Alternatively, the tab may also be oriented at least partially at an angle to the plate plane. In one embodiment, the tab is arranged on an outer edge of the plate body. The tab may be configured for example as an overhang which projects laterally from the plate body. The bipolar plate may have at least one through-opening for the passage of a fluid. The tab may be arranged for example on an inner edge of such a through-opening. The common edge of the tab and edge of the plate body may take up only part of the length of the edge of the plate body in question, for example up to one-third or up to half of the length of an inner edge of a through-opening or up to one-twentieth of the length of a circumferential outer edge of the plate body or up to one-eighth of the length of one outer edge, that is to say one side edge, of the plate body.

The predetermined breaking point is usually designed such that a defined separation of the tab along the predetermined breaking point is possible. The defined separation makes it possible largely to avoid damage to the bipolar plate and/or to the tab after separation of the tab. It may be provided that a stiffening structure, which extends at least partially along the predetermined breaking point, for separating the tab in a defined manner along the predetermined breaking point is arranged on at least one side of the predetermined breaking point, which may be arranged on both sides of the predetermined breaking point. In addition, or as an alternative, the tab may have at least one further stiffening structure for stiffening the tab. In this case, the respective stiffening structure may be configured as an embossed structure, a bead, or a group of embossings. The bead may be configured for example as a half-bead or as a full bead. Furthermore, domes or nubs may be provided as embossed structures, which may be arranged for example in at least one row.

The predetermined breaking point may for example comprise at least one indentation and/or at least one perforation. A plurality of spaced-apart indentations and/or perforations, arranged in a row, may also be provided. In the context of this document, the perforation is configured as a through-opening, while the indentation is configured as material weakenings which do not penetrate all the way through. The predetermined breaking point is usually configured as a predetermined breaking line and may extend for example in an arc shape or in a straight line in the longitudinal direction or may be composed of arc-shaped and/or straight portions arranged next to one another in a row.

Optionally, the tab has a first coding which is associated with the respective separator plate and/or with the bipolar plate. In this case, the first coding of the tab may be used as an identification feature of the corresponding bipolar plate. Often, the separator plate and/or the bipolar plate has a second coding which corresponds to the first coding on the tab. The respective coding (that is to say the first and/or second coding) thus enables a traceability of the bipolar plate, for example after production of the bipolar plate. In some embodiments, the respective coding comprises an inscription and/or a pattern. The pattern may in turn be configured as a barcode, a 2D code, such as a data matrix code or QR code, a coloured pattern, a punched pattern and/or an embossed pattern. The respective coding may also comprise a chip, such as an RFID chip. By way of example, the batch of plate material used can be traced in this way.

Optionally, the tab may have at least one process monitoring area. The at least one process monitoring area may be arranged on one side of a flat surface of the tab, or on both sides of the tab. Elements which can be checked during and/or after production of the bipolar plate, and which thus make it possible to monitor certain process parameters, may be incorporated in or applied to the process monitoring area of the tab. The element incorporated in or applied to the process monitoring area is usually present in an identical, representative or at least similar form on the plate body of the separator plate or bipolar plate, so that test results of the process monitoring area are transferable to the separator plate or bipolar plate; this is true because the tab and the rest of the plate body are made of the same material from the same batch. By way of example, the tab may be tested directly after production of the associated bipolar plate and before the bipolar plate is installed in an electrochemical system. This can prevent low-quality bipolar plates from being installed in the system. The process monitoring area may for example have a coating, a surface treatment and/or a structuring.

The at least one process monitoring area may for example have a coating, for example a sealing coating, an adhesive coating, an electrically conductive coating, or an anti-corrosion coating. The coating may comprise a coating applied by screen printing, a coating applied by a knife, a spray coating, a coating applied by PVD (physical vapour deposition), a coating applied by CVD (chemical vapour deposition), and/or a coating applied by pad printing. Furthermore, the process monitoring area may comprise a punched structure or a shaped structure, for example an embossed structure such as a bead or a channel structure. The shaped structure may be formed in the tab by embossing, deep drawing or hydroforming. Furthermore, the process monitoring area may have a laser structuring, which has been produced by means of a laser, or a melt structure, which has been produced by melting the tab material. In addition, the process monitoring area may be treated with a solvent, a cleaning agent, or a plasma.

In addition or as an alternative to the explicit elements incorporated in or applied to the surface, the tab can also be used to check the sheet-metal material per se. In this case, at least a portion of the process monitoring area may remain at least untreated and uncoated in order to test the sheet-metal material.

It is possible by means of the tab to replicate at least some or even all of the processing steps under identical processing conditions on the identical plate material.

As described above, it is possible that just one separator plate has the tab. However, it may also be provided that each of the two separator plates of a bipolar plate has the aforementioned at least one tab. The tabs may be arranged at different locations on the respective separator plates. Optionally, the tabs may at least partially or entirely overlap in a direction perpendicular to a plate plane of the bipolar plate. Sometimes, the tabs of the separator plates may touch one another, for example in a contact area. To check the quality of the connection of the two separator plates, the separable overlapping tabs may likewise be connected to one another. After separating the tabs, the connection of the tabs can then provide information and conclusions about the connection between the two separator plates. In one possible embodiment, the tabs are connected to one another by means of a material bond. The material bond may be provided in the process monitoring areas provided for this purpose. Possible material bonds include welded joints, soldered joints and/or adhesive bonds.

Each of the separator plates or flow plates may be made of a metal sheet, metals such as stainless steel and/or titanium being suitable for the metal sheet. The tab and the plate body of the at least one separator plate are made of the same base material. However, a surface structure of the tab may differ locally from a surface structure of the plate body, cf. what has been stated above in relation to the process monitoring area.

While a tab formed on the outer edge of the separator plate or bipolar plate may in theory still remain on the outer edge also during operation of a fuel cell system, embodiments of a tab formed on the inner edge of a through-opening of the separator plate or bipolar plate must be separated at the latest just prior to commissioning of the fuel cell system.

According to a further aspect, a retention sample of a bipolar plate for an electrochemical system is provided. The retention sample comprises a tab with a first breaking edge which can be separated from the bipolar plate via a predetermined breaking point. In other words, the predetermined breaking point extends along the first breaking edge. The tab has a process monitoring area and/or a first coding which is associated with the bipolar plate and/or with a separator plate of the bipolar plate. The bipolar plate may correspond to the bipolar plate mentioned above, the tab being separated from the bipolar plate and used as a retention sample. The retention sample enables a traceability of the bipolar plate after production thereof. The retention sample enables substitutional representative analyses of elements of the bipolar plate at the manufacturer if the finished bipolar plates have already been delivered to the customer or installed at the customer. There is thus no need for the bipolar plates to be returned to the manufacturer.

According to a further aspect, a system is provided which comprises the aforementioned retention sample and the associated bipolar plate for an electrochemical system. The bipolar plate comprises two separator plates which are connected to one another, the bipolar plate having a second breaking edge which has a shape complementary to the first breaking edge. The first breaking edge and/or second breaking edge may in each case have an edge geometry that is characteristic for the type of separation used (laser, power surge, cutting, etc.).

What has been stated above applies not only to the plurality of identical bipolar plates, as used in a fuel cell stack, but also to the individual flow plates of the respective last pair of separator plates in the stack, that is to say to so-called unipolar plates. At least one of the flow plates of this pair of separator plates may have some differing properties compared to the aforementioned separator plates, but may likewise have at least one tab for the various purposes mentioned above.

According to a further aspect, a flow plate for an electrochemical system is proposed, the flow plate having a plate body and at least one tab which is formed in one piece with the plate body and can be separated from the plate body via a predetermined breaking point.

While the bipolar plate described above has two separator plates which are connected to one another, the flow plate mentioned here need not necessarily be provided with two plates which are connected to one another. The flow plate may be configured as a one-layer plate, for example a one-layer separator plate. Above-described features of the predetermined breaking point, of the tab and/or of the retention sample, which are disclosed in connection with the bipolar plate and/or the separator plates, may also be combined with the flow plate in so far as they are compatible with use in a one-layer single plate. The abovementioned retention sample and the abovementioned system can also be used and with the flow plate. The flow plate may be configured for example as a unipolar plate, a bipolar plate, a humidifier plate and/or a separator plate. The flow plate may be made for example of a metal or a plastic.

Also proposed is an electrochemical system which comprises a plurality of stacked bipolar plates and/or flow plates of the type described above. The electrochemical system may be, for example, a fuel cell system, an electrochemical compressor, a redox flow battery, a humidifier for another electrochemical system, or an electrolyser.

A method for producing a bipolar plate is also proposed. The method comprises the steps:
providing a plate,
forming a first separator plate having a plate body and at least one tab formed in one piece with the plate body,
introducing a material weakening into the first separator plate so as to form a predetermined breaking point, via which the tab can be separated from the plate body,
providing a second separator plate,
forming the bipolar plate by connecting the first separator plate to the second separator plate.

The method may then comprise the additional step:
separating the tab from the first separator plate along the predetermined breaking point.

By separating the tab, the abovementioned retention sample can be obtained. The tab may be separated by applying energy such as heat, for example laser radiation, a power surge, or induction. To this end, use can be made of a suitable energy source, for example a laser, a current source or an induction source. One advantage of said procedure is that sharp edges and burrs, which typically occur in the case of mechanical separation, can be avoided. Alternatively, the tab may be mechanically or chemically separated. Usually, the tab is not separated from the respective separator plate until the two separator plates have been connected.

A method for producing a flow plate for an electrochemical system is also provided. The method comprises the steps:
providing a plate,
forming a flow plate having a plate body and at least one tab formed in one piece with the plate body,
introducing a material weakening into the flow plate so as to form a predetermined breaking point, via which the tab can be separated from the plate body.

The tab can then be separated from the flow plate along the predetermined breaking point, for example in the manner described above.

A flow field is often integrally formed in the flow plate, for example by embossing, hydroforming and/or deep drawing. The flow field usually comprises a plurality of channels and/or webs, which are designed to guide a fluid along the flow plate. Typically, the tab is not separated from the flow plate until after the flow field has been formed.

The separation may take place when all the production steps during production of the flow plate, separator plate and/or bipolar plate have already been executed. However, it is also possible that the separation step takes place after some of the production steps have been completed. Although it is possible in principle that the tab is separated from a row of plates (separator plates, flow plates and/or bipolar plates) which are still joined together in a strip material, the separation may take place when the plates are already in the form of individual plates, that is to say plates that have been separated from a strip material.

The methods are suitable for producing the bipolar plate, flow plate and/or retention sample described above. Features that have been described only in connection with the bipolar plate, flow plate and/or retention sample can also be claimed for the methods, and vice versa.

A method for testing a retention sample of a bipolar plate or flow plate is also proposed. The bipolar plate comprises two separator plates which are connected to one another, at least one of the separator plates having a plate body and at least one tab which is formed in one piece with the plate body and can be separated from the plate body via a predetermined breaking point. The flow plate comprises a plate body and at least one tab which is formed in one piece with the plate body and can be separated from the plate body via a predetermined breaking point.

The tab is connected to the plate body while the bipolar plate or flow plate is being produced and then is separated from the plate body. The tab may be connected to the bipolar plate or flow plate throughout the entire duration of production.

In addition, the separated tab is designed as the retention sample of the bipolar plate or flow plate. The method comprises the following step:

testing at least one material property or one processing parameter of the tab.

In a further step, conclusions can be drawn about the nature of the bipolar plate or flow plate, for example the surface thereof, based on the retention sample. It should be noted here that the steps of separating and testing can be carried out directly one after the other, so that both steps can be carried out for example within one day or within one hour or less. However, the step of testing may also take place later, for example at the manufacturer, while the bipolar plate or flow plate is located at a purchaser or customer. Consequently, any complaints can be followed up and evaluated. A traceable coding (cf. the first coding mentioned above) may further contribute to the temporally offset analysis of the retention sample.

On the whole, the retention sample can provide a specimen of the bipolar plate or flow plate that has gone through the same processing steps as the bipolar plate or flow plate. Properties of the bipolar plate or flow plate can thus be examined on the basis of the retention sample, without the bipolar plate or flow plate itself having to be examined. The tab may be tested non-destructively. It may also be provided that a destructive testing of the tab takes place. In the case of destructive testing, examining the retention sample has the advantage that the bipolar plate or flow plate need not be destroyed or damaged. The same also applies to a flow plate or a separator plate prior to assembling two separator plates to form a bipolar plate.

It may be provided that the at least one tab has at least one process monitoring area, the process monitoring area and the plate body each being structured, treated and/or coated during production of the flow plate, separator plate or bipolar plate.

Features of the production method and of the test method can be combined with one another. Features of the bipolar plate, the flow plate, the retention sample and the system can also be combined with the test method, and vice versa.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE FIGURES

Exemplary embodiments of the present disclosure will be explained in greater detail below on the basis of appended figures.

FIGS. 1-11 are shown approximately to scale.

In the following description and in the figures, recurring and functionally identical features are provided with the same reference signs.

DETAILED DESCRIPTION

Figure 1:
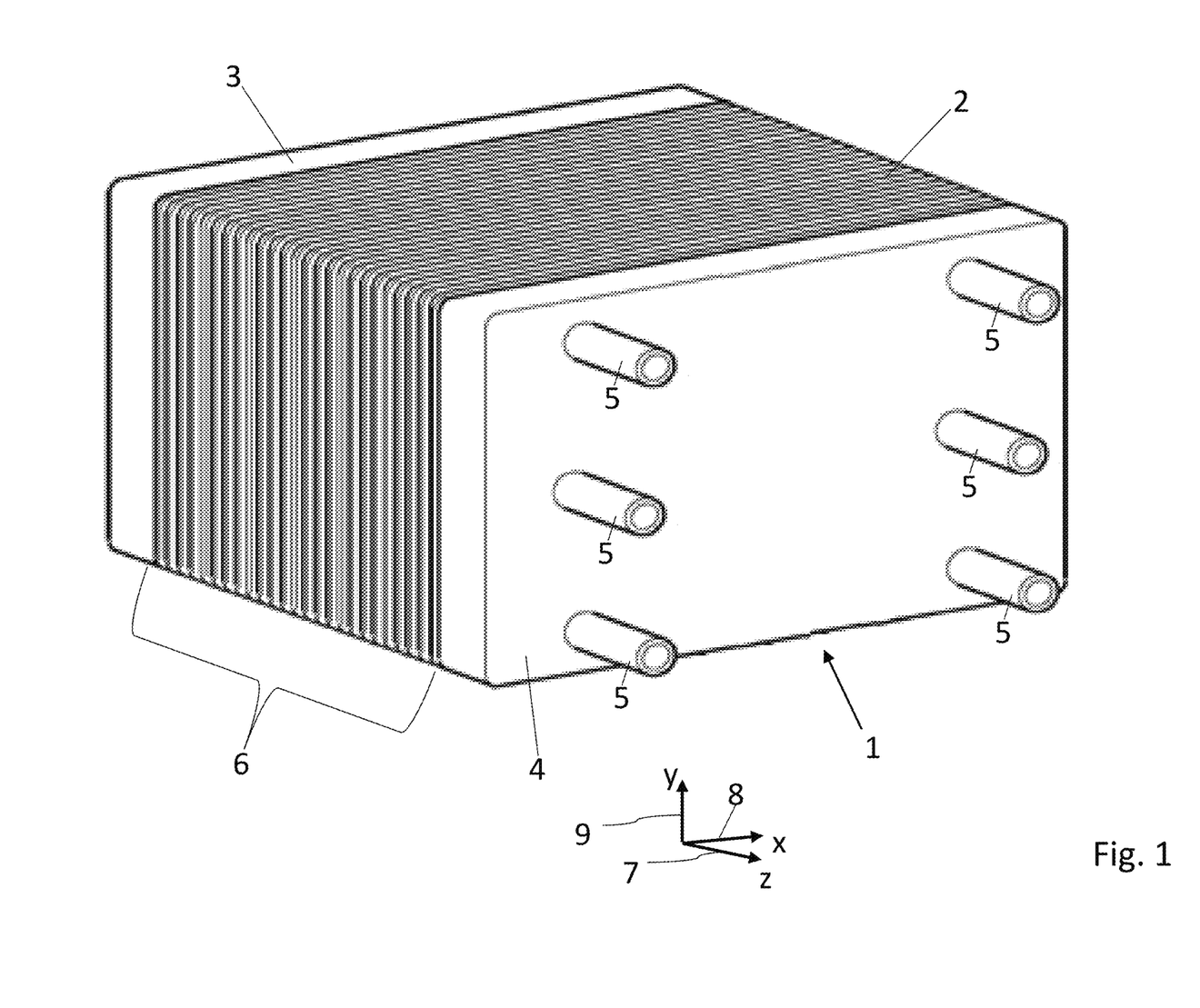
FIG. 1 schematically shows, in a perspective view, an electrochemical system comprising a plurality of separator plates or bipolar plates arranged in a stack.

FIG. 1 shows an electrochemical system 1 comprising a plurality of structurally identical metal bipolar plates 2, which are arranged in a stack 6 and are stacked along a z-direction 7. The bipolar plates 2 of the stack 6 are clamped between two end plates 3, 4. The z-direction 7 will also be referred to as the stacking direction. In the present example, the system 1 is a fuel cell stack. Each two adjacent bipolar plates 2 of the stack therefore enclose between them an electrochemical cell, which serves for example to convert chemical energy into electrical energy. To form the electrochemical cells of the system 1, a membrane electrode assembly (MEA) 10 is arranged in each case between adjacent bipolar plates 2 of the stack (see for example FIG. 2). Each MEA typically contains at least one membrane, for example an electrolyte membrane together with electrodes. Furthermore, a gas diffusion layer (GDL) may be arranged on one or both surfaces of the MEA.

In alternative embodiments, the system 1 may also be configured as an electrolyser, as an electrochemical compressor, as a humidifier for an electrochemical system, or as a redox flow battery. Bipolar plates can likewise be used in these electrochemical systems. The structure of these bipolar plates may then correspond to the structure of the bipolar plates 2 explained in detail here, although the media guided on and/or through the bipolar plates in the case of an electrolyser, an electrochemical compressor, a humidifier for an electrochemical system, or a redox flow battery may differ in each case from the media used for a fuel cell system.

The z-axis 7, together with an x-axis 8 and a y-axis 9, spans a right-handed Cartesian coordinate system. The bipolar plates 2 each define a plate plane, each of the plate planes of the separator plates being oriented parallel to the x-y plane and thus perpendicular to the stacking direction or to the z-axis 7. The end plate 4 has a plurality of media ports 5, via which media can be fed to the system 1 and via which media can be discharged from the system 1. Said media that can be fed to the system 1 and discharged from the system 1 may comprise for example fuels such as molecular hydrogen or methanol, reaction gases such as air or oxygen, reaction products such as water vapour or depleted fuels, or coolants such as water and/or glycol.

Figure 2:
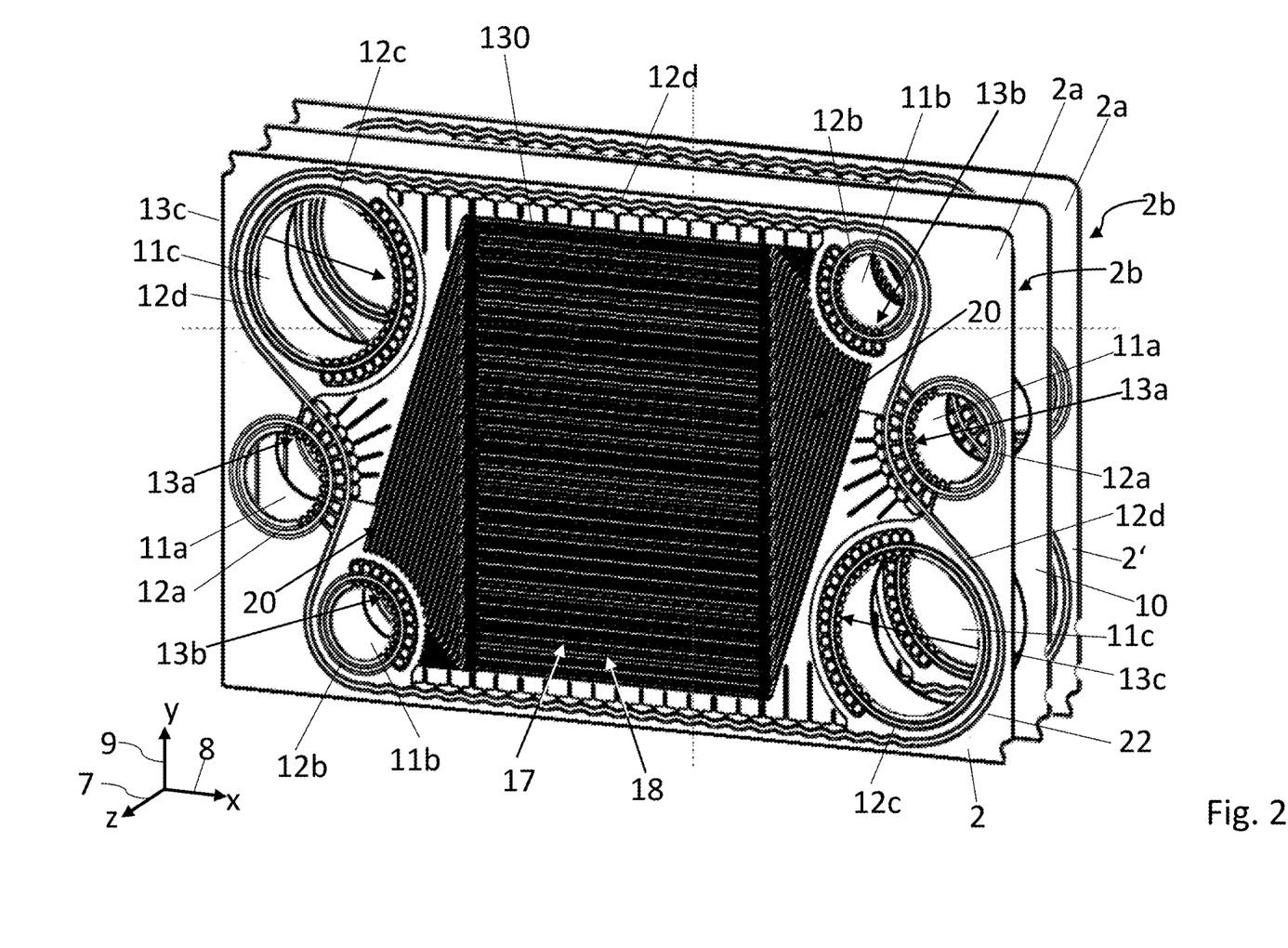
FIG. 2 schematically shows, in a perspective view, two bipolar plates of the system according to FIG. 1 with a membrane electrode assembly (MEA) arranged between the bipolar plates.

FIG. 2 shows, in a perspective view, two adjacent bipolar plates 2, 2' of an electrochemical system of the same type as the system 1 from FIG. 1, as well as a membrane electrode assembly (MEA) 10 which is arranged between said adjacent bipolar plates 2, 2', the MEA 10 in FIG. 2 being largely obscured or covered by the bipolar plate 2 facing towards the viewer. The bipolar plate 2 is formed of two separator plates 2a, 2b which are joined together by a material bond, of which only the first separator plate 2a facing towards the viewer is visible in FIG. 2, said first separator plate obscuring or covering the second separator plate 2b. The separator plates 2a, 2b are generally formed as individual plates, which are each manufactured from a metal sheet, for example from a stainless-steel sheet. The separator plates 2a, 2b are usually connected to one another by a material bond and may for example be welded to one another, for example by laser welding.

The separator plates 2a, 2b typically have through-openings, which are aligned with one another and form through-openings 11a-c of the bipolar plate 2. When a plurality of bipolar plates of the same type as the bipolar plate 2 are stacked, the through-openings 11a-c form lines which extend through the stack 6 in the stacking direction 7 (see FIG. 1). Usually, each of the lines formed by the through-openings 11a-c is fluidically connected to one of the ports 5 in the end plate 4 of the system 1. For example, coolant can be introduced into the stack or discharged from the stack via the lines formed by the through-openings 11a. In contrast, the lines formed by the through-openings 11b, 11c may be configured to supply fuel and reaction gas to the electrochemical cells of the fuel cell stack 6 of the system 1 and to discharge the reaction products from the stack. The media-guiding through-openings 11a-11c are substantially parallel to the plate plane.

In order to seal off the through-openings 11a-c with respect to the interior of the stack 6 and with respect to the surrounding environment, the first separator plates 2a usually have sealing arrangements, here in the form of sealing beads 12a-c, which are each arranged around the through-openings 11a-c and in each case completely surround the through-openings 11a-c. On the rear side of the bipolar plates 2, facing away from the viewer of FIG. 2, the second separator plates 2b have corresponding sealing beads for sealing off the through-openings 11a-c (not shown).

In an electrochemically active region 18, the first separator plates 2a have, on the front side thereof facing towards the viewer of FIG. 2, a flow field 17 with structures for guiding a reaction medium along the front side of the separator plate 2a. In FIG. 2, these structures are defined by a plurality of webs and channels extending between the webs and delimited by the webs. The electrochemically active region 18 may have at least one coating in some regions, for example in the region of the webs, or across the entire surface. A corrosion-reducing coating may be provided across the entire surface, and/or a conductivity-improving coating 130 may be provided at least in some regions. On the front side of the bipolar plates 2, 2' facing towards the viewer of FIG. 2, each of the first separator plates 2a additionally has a distribution or collection region 20. The distribution or collection region 20 comprises structures which are configured to distribute over the active region 18 a medium that is introduced into the distribution or collection region 20 from a first of the two through-openings 11b, and/or to collect or to pool a medium flowing towards the second of the through-openings 11b from the active region 18. In FIG. 2, the distributing structures of the distribution or collection region 20 are likewise defined by webs and channels extending between the webs and delimited by the webs. In general, the elements 17, 18, 20 can therefore be understood as media-conducting embossed structures.

The sealing beads 12a-12c usually have passages 13a-13c, which here are configured as local elevations of the bead, of which the passages 13a are formed both on the underside of the upper separator plate 2a (the separator plate facing towards the viewer) and on the upper side of the lower separator plate 2b (the separator plate facing away from the viewer), while the passages 13b are formed in the upper separator plate 2a and the passages 13c are formed in the lower separator plate 2b. By way of example, the passages 13a enable a passage of coolant between the through-opening 11a and the distribution region, so that the coolant reaches the distribution region between the separator plates and is guided out therefrom. Furthermore, the passages 13b enable a passage of hydrogen between the through-opening 11b and the distribution region 20 on the upper side of the upper separator plate 2a; these passages 13b are characterized by perforations facing towards the distribution region and extending at an angle to the plate plane. Therefore, hydrogen for example flows through the passages 13b from the through-opening 11b to the distribution region on the upper side of the upper separator plate 2a, or in the opposite direction. The passages 13c enable a passage of air for example between the through-opening 11c and the distribution region, so that air reaches the distribution region on the underside of the lower separator plate 2b and is guided out therefrom. The associated perforations are not visible here.

The first separator plates 2a also typically each have a further sealing arrangement, here in the form of a perimeter bead 12d, which extends around the flow field 17 of the active region 18, the distribution or collection region 20 and the through-openings 11b, 11c and seals these off with respect to the through-opening 11a, that is to say with respect to the coolant circuit, and with respect to the environment surrounding the system 1. The second separator plates 2b each comprise corresponding perimeter beads. The structures of the active region 18, the distributing structures of the distribution or collection region 20 and the sealing beads 12a-d are each formed in one piece with the separator plates 2a and are integrally formed in the separator plates 2a, for example in an embossing, hydroforming or deep-drawing process. The same applies to the corresponding distributing structures and sealing beads of the second separator plates 2b. A predominantly unstructured outer edge region 22 is obtained in each separator plate 2a, 2b outside of the region enclosed by the perimeter bead 12b.

At least some of the aforementioned sealing beads may be at least partially coated on at least one of their surface(s), for example at least on a bead top. A polymer-based coating which improves the micro-sealing is suitable for this purpose. A pre-treatment, such as for example a cleaning step or a surface treatment, may be carried out before the coating is applied.

Figure 10:
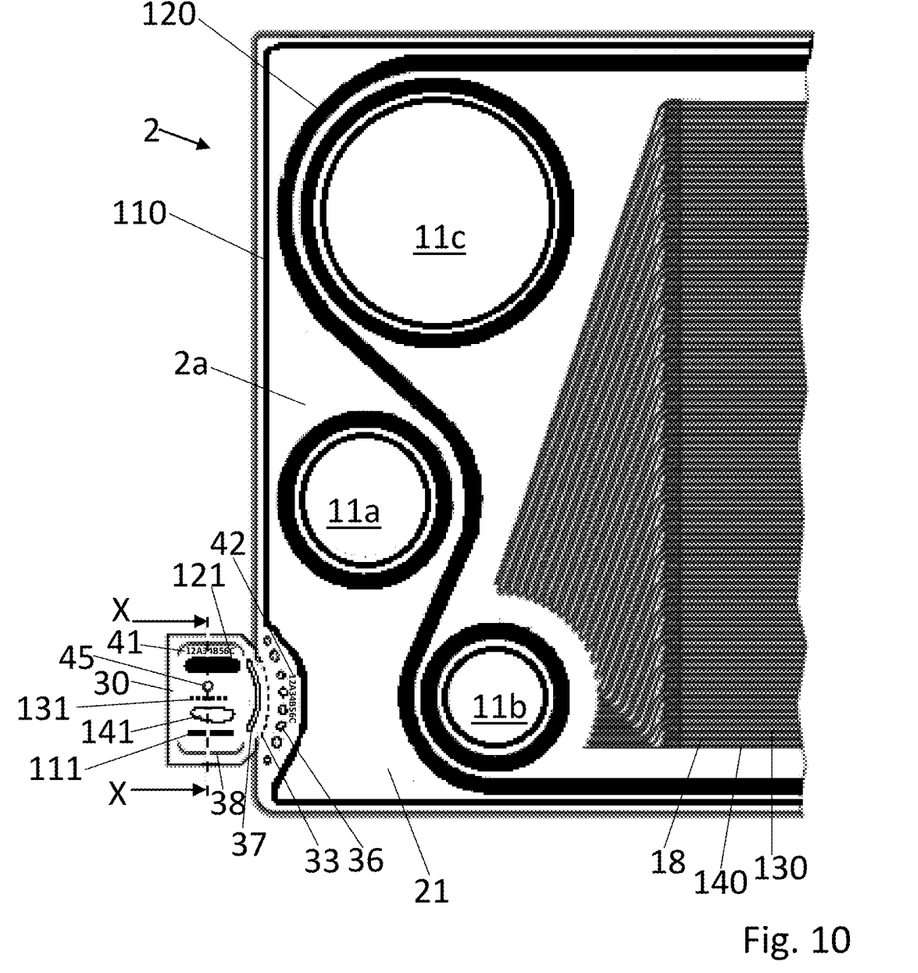
FIG. 10 schematically shows a plan view of part of a bipolar plate with two separable tabs arranged entirely one above the other.
Figure 11:
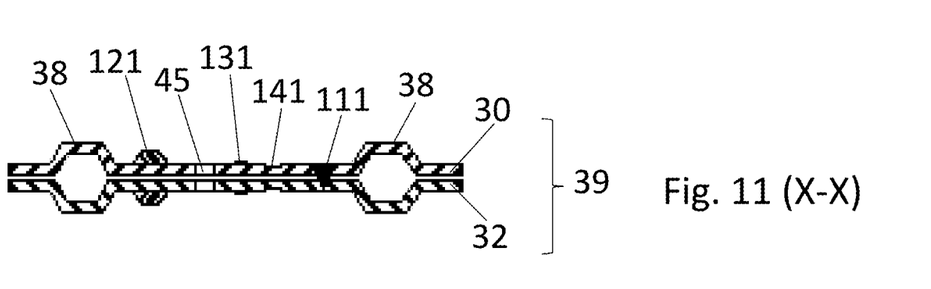
FIG. 11 schematically shows a section along the section line X-X of FIG. 10.

As an alternative to the aforementioned sealing beads formed in one piece with the separator plates, other sealing elements can also be used, for example sealing profiles inserted in a depression of the surface or sealing profiles 120 applied to the surface, as shown in FIGS. 10 and 11.

Each of the separator plates 2a, 2b is typically formed from a metal sheet having a sheet thickness between 60 μm and 150 μm. Due to the small thickness of the individual plates 2a, 2b on the one hand and the relatively large size of the plates in the y- and x-direction on the other hand, the plates 2, 2a, 2b can be mechanically deformed and damaged relatively easily. However, due to the many functional areas, for example the flow field 17, the active region 18, the distribution or collection region 20, the through-openings 11a-c and the bead arrangements 12a-d, the plates 2, 2a, 2b should only be handled in the largely unstructured edge region 22 thereof, so as to avoid contamination of the plates 2, 2a, 2b. On the whole, therefore, the plates 2, 2a, 2b may therefore be difficult to handle; this applies both to manual handling and to handling by means of automatic gripper systems.

Figure 3:
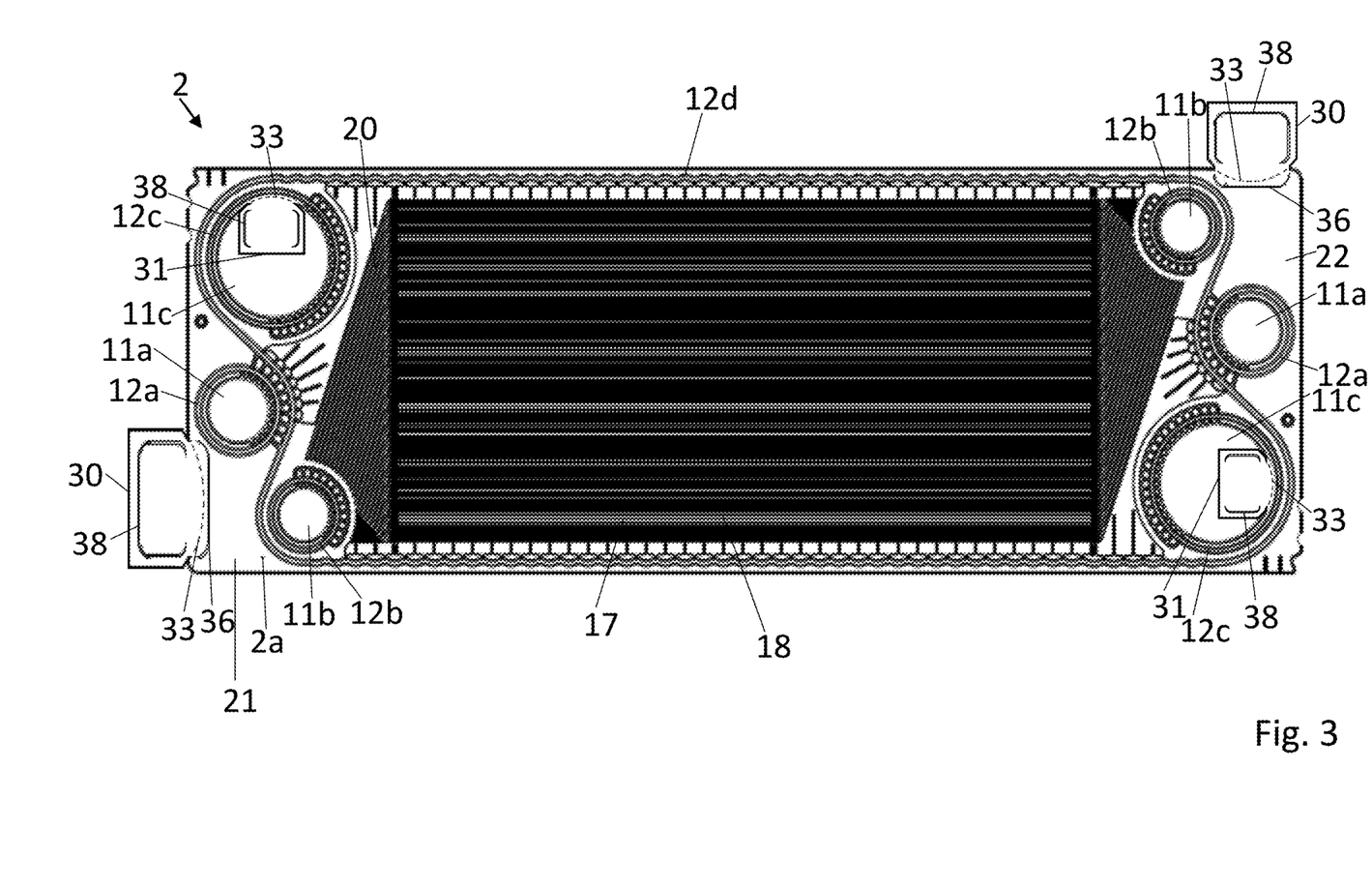
FIG. 3 schematically shows a plan view of a bipolar plate with multiple separable tabs, which can be used in the stack of FIG. 1.

FIG. 3 schematically shows a plan view of a bipolar plate 2 comprising separator plates 2a, 2b, which can be used in the stack 6 of the electrochemical system 1. Only the first separator plate 2a can be seen in FIG. 3 since this plate completely covers the second separator plate 2b. In contrast to the plates shown in FIG. 2, the separator plate 2a comprises a plate body 21 and additionally at least one tab 30, 31. The tab 30, 31 is formed in one piece with the plate body 21 and can be separated from the plate body 21 via a predetermined breaking point 33.

In the exemplary embodiments of FIGS. 3-11, the tab 30, 31 extends parallel to a plate plane defined by the plate body 21. In alternative embodiments, the tab 30, 31 may also be arranged at an angle to the plate plane. The tab 30, 31 may be arranged at different locations on the bipolar plate. By way of example, the tab 30 is arranged on an outer edge of the bipolar plate 2 and projects laterally from the plate body 21, as a result of which a relatively large amount of space is available for the tab 30 and the separation of the tab 30 and the handling of the tab 30 are relatively easy. The tab 31 is arranged on an inner edge of the through-opening 11c. Consequently, material of the metal sheet that would otherwise have been thrown away when producing the through-opening 11c can be used to produce the tab 31 in the through-opening 11c.

Figure 6:
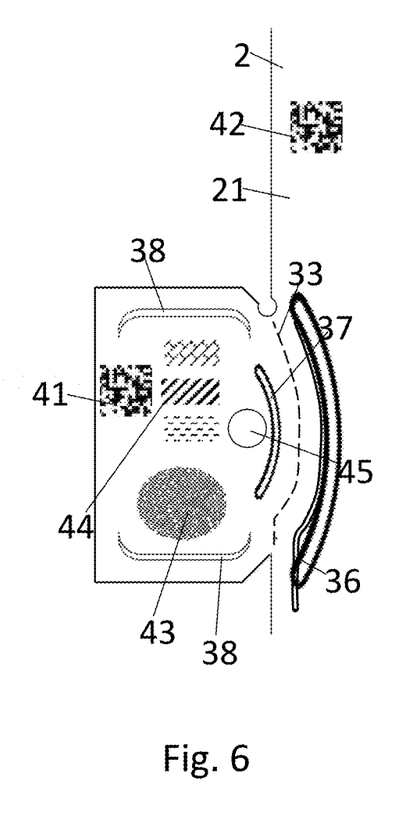
FIG. 6 schematically shows a detail view of a tab, which is connected to a bipolar plate via a predetermined breaking point.
Figure 7A:
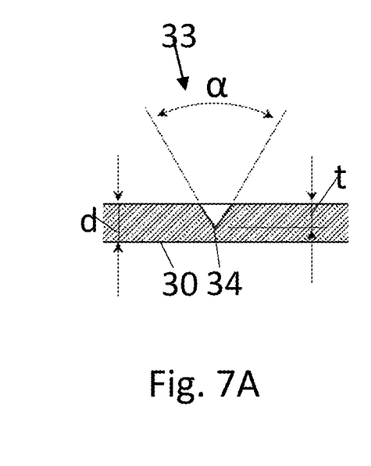
FIGS. 7A, 7B, 7C, schematically show sectional views of possible predetermined breaking points of FIG. 6.
Figure 7B:
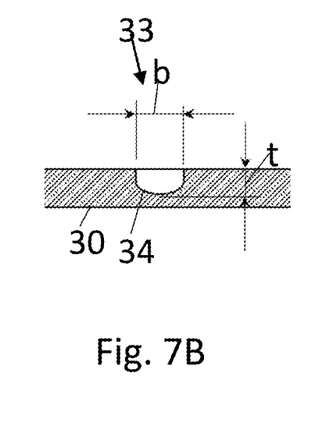
Figure 7C:
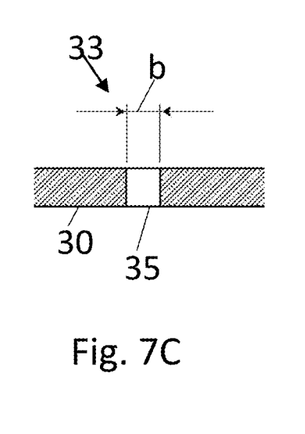

FIGS. 5 and 7A-C show sections through various predetermined breaking points 33. The predetermined breaking point 33 has a width b measured perpendicular to a direction of longitudinal extension of the predetermined breaking point 33. Accordingly, the predetermined breaking point 33 may have an indentation 34 which is for example V-shaped with an opening angle a (FIG. 7A) or U-shaped with a maximum width b (FIG. 7B). The indentation 34 is designed here as a material weakening of maximum depth t, a residual thickness of the material being formed by the difference between the thickness d of the tab 30 and the depth t of the indentation 34. The predetermined breaking point 33 may alternatively or additionally also have a plurality of through-perforations 35 of diameter b (FIG. 7C). The predetermined breaking point 33 may be formed for example by engraving, punching, laser radiation, or burning using current. As shown in FIGS. 3, 4, 6, 8 and 10, the predetermined breaking point 33 may open into a widening cutout between the tab 30 and the plate body 21. The predetermined breaking point 33 may extend along the plate plane in a predominantly arc-shaped manner.

In order to make it easier to separate the tab along the predetermined breaking point 33 and not to damage the bipolar plate 2, at least one stiffening structure 36, 37, 12c may be provided, which extends along the predetermined breaking point 33. In the tab 30 of FIG. 3, a stiffening structure 36 is provided on the plate body 21, while the tab 30 of FIGS. 4, 6 and 8 has stiffening structures 36, 37 on the plate body 21 and the tab 30 on both sides of the predetermined breaking point 33. In the tab 31 of FIGS. 3 and 4, the bead arrangement 12c of the through-opening 11c forms the stiffening structure. The tab 30, 31 may have at least one stiffening structure 38 for reinforcing the tab 30, 31. Said stiffening structures 36, 37, 38 may be designed as embossed structures such as beads (see FIGS. 3-9), nubs or domes (see FIG. 10).

The tab 30, 31 may for example facilitate the handling of the bipolar plate 2 or of the individual separator plates 2a, 2b. Often, the tab 30, 31 is configured for transporting, positioning, holding and/or gripping the bipolar plate 2 or the individual separator plates 2a, 2b. By way of example, the tab 30, 31 has a substantially flat or structured holding area 43, at which the tab 30, 31 can be handled and held, without the plate body 21 of the separator plate 2a, 2b being contaminated or mechanically deformed. This is symbolized in FIGS. 4, 6 and 8 by a fingerprint. The holding area 43 can also be held by a suction lifting tool, other lifting tool or suction cup. As a further measure for transporting, holding, positioning and gripping, the tab 30, 31 may have a positioning opening 45 for receiving a centring pin of a centring device or for checking the relative position of the two separator plates 2a, 2b of a bipolar plate 2. The predetermined breaking point 33 may be configured such that it does not break or plastically deform under the weight of the bipolar plate 2.

The tab 30, 31 may be designed as a retention sample. To this end, the tab 30, 31 is separated from the bipolar plate 2 and stored. The separation along the predetermined breaking point 33 leads to breaking edges both on the side of the tab 30, 31 and on the side of the bipolar plate. The tab 30, 31 separated from the bipolar plate 2 and designed as a retention sample therefore has a first breaking edge, which has a shape complementary to a second breaking edge of the bipolar plate 2. The tab 30, 31 designed as a retention sample can enable a traceability of the bipolar plate 2. A system consisting of the retention sample 30, 31 and the bipolar plate 2 can be formed, which can be used for quality control.

Figure 4:
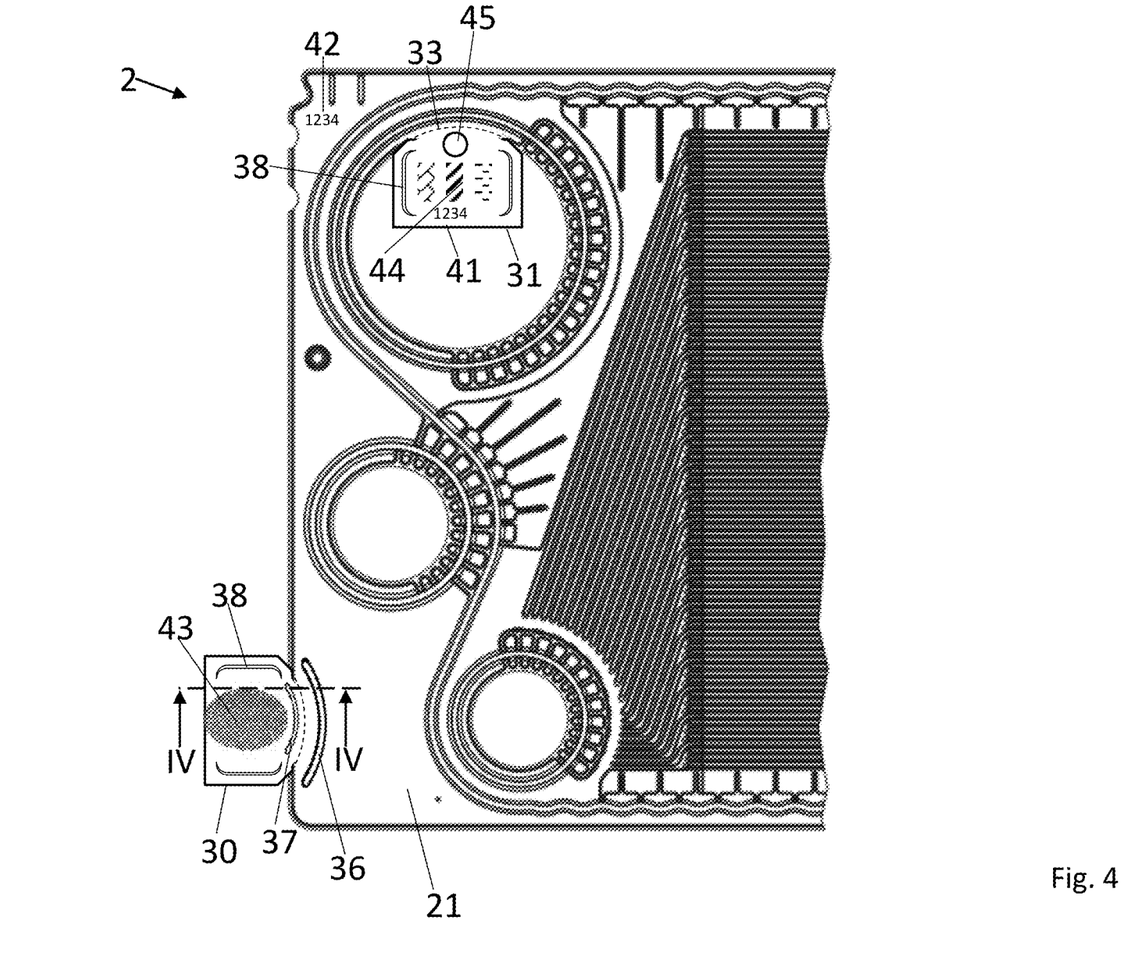
FIG. 4 schematically shows a plan view of part of a bipolar plate with multiple separable tabs, which can be used in the stack of FIG. 1.
Figure 5:
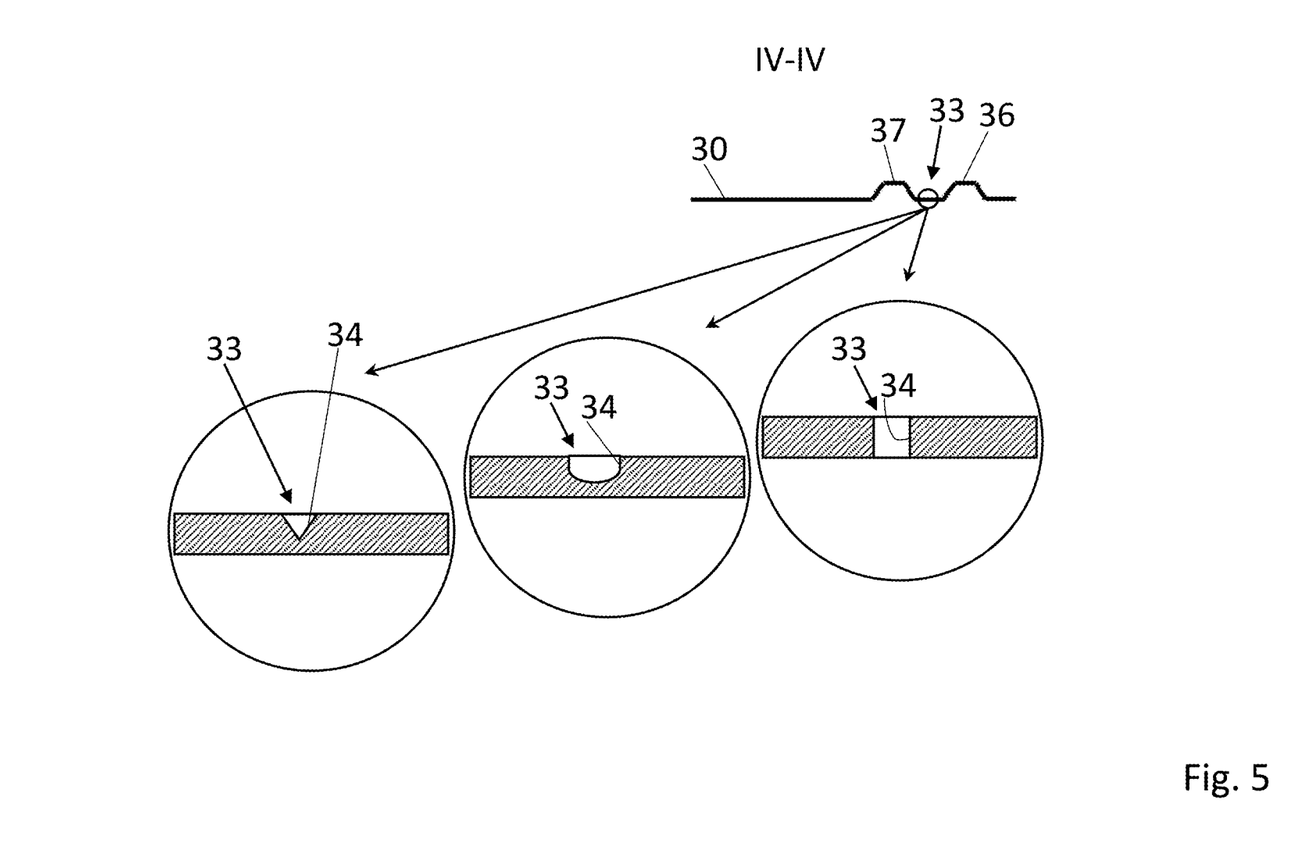
FIG. 5 schematically shows a section through a portion of the bipolar plate of FIG. 4.

To simplify the traceability, the tab 30, 31 may have a first coding 41, which is associated with the bipolar plate 2 (see FIGS. 4, 6 and 10). In addition, the bipolar plate 2 may have a second coding 42, which is associated with the tab 30, 31 and corresponds to the first coding 41. In the exemplary embodiments of FIGS. 4 and 10, the respective coding 41, 42 is configured as an inscription, for example a numerical code, but it may alternatively or additionally be configured as a pattern such as a barcode, a 2D code, for example a data matrix code or a QR code as in FIG. 6, or as a coloured pattern, a punched pattern and/or an embossed pattern. The respective coding 41, 42 may also comprise a chip such as an RFID.

In the embodiments of FIGS. 4, 6 and 10, the tab 30, 31 comprises at least one process monitoring area 44. By way of example, multiple process monitoring areas 44 may be provided on one side or on both sides of the tab 30, 31. At least one surface treatment 141 (which here has a slightly ablating effect), coating 121, 131 (in the example of FIGS. 10 and 11, an applied sealing element is also to be regarded as a sealing coating 121) and/or structuring may be applied to or incorporated in the process monitoring area 44 and may likewise be carried out at least in a portion of the bipolar plate 2, namely as a surface treatment 140, as a profile-shaped sealing coating 120 and as a conductivity coating 130. Suitable coatings include, for example, a sealing coating 120, 121, here a sealing profile, an adhesive coating, an electrically conductive coating 130, 131, or an anti-corrosion coating. The at least one coating 121, 131 may be a coating applied by screen printing, a coating applied by a knife, a spray coating, a coating applied by PVD (physical vapour deposition), a coating applied by CVD (chemical vapour deposition), and/or a coating applied by pad printing. Such coatings are often carried out on bipolar plates 2 or separator plates 2a, 2b. Suitable structurings include for example an embossed structure, a laser structuring and/or a melt structure. Suitable surface treatments are a treatment of the tab surface with a solvent, a cleaning agent, or a plasma. Reference sign 44 has been omitted in FIG. 10; the elements 111 (laser weld seam), 121 (sealing coating, sealing profile), 131 (conductivity coating) and 141 (pre-treatment) each represent a process monitoring area for analogous elements in the plate body, which are denoted there by the reference signs 110 (laser weld seam), 120 (sealing coating, sealing profile), 130 (conductivity coating) and 140 (pre-treatment).

In addition, or as an alternative to the explicit elements incorporated in or applied to the process monitoring area 44, the process monitoring area 44 can also be used to check the sheet-metal material of the separator plates 2a, 2b. In this case, at least a portion of the process monitoring area 44 may remain unstructured, untreated and uncoated in order to test the sheet-metal material.

By means of the process monitoring area 44, a subsequent indirect analysis of the bipolar plate 2 can be carried out without having to remove the bipolar plate 2 that has already been installed in the electrochemical system 1. For this, both non-destructive and destructive analyses of the tab 30, 31 are possible.

The base material of the tab 30, 31, 32 and the base material of the plate body 21 are identical. However, it may be that the surface structure of the tab, for example of the process monitoring area 44, differs locally from the surface structure of the plate body 21.

Figure 8:
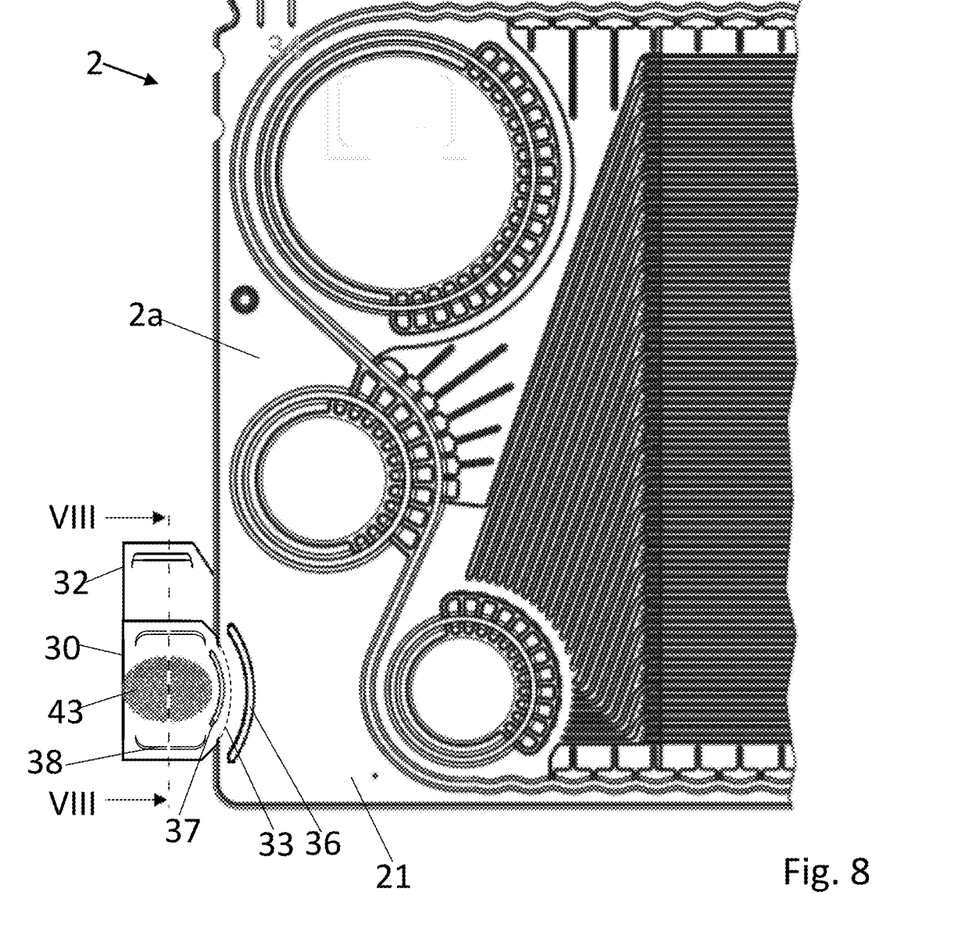
FIG. 8 schematically shows a plan view of part of a bipolar plate with two separable tabs arranged partially one above the other.
Figure 9:
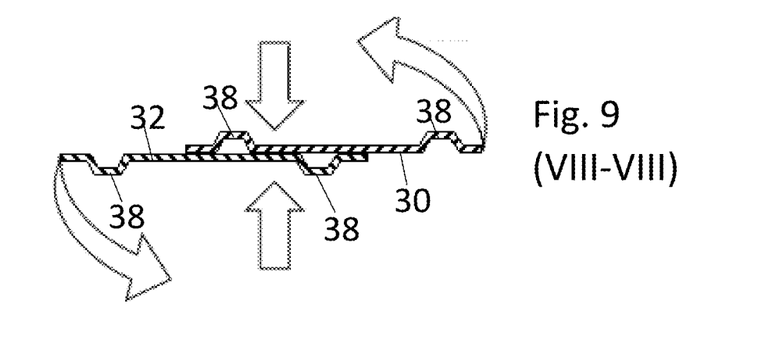
FIG. 9 schematically shows a section along the section line VIII-VIII of FIG. 8, as well as method steps for separating the tabs of the bipolar plate of FIG. 8.

The tab 30, 31 may be provided in just one of the two separator plates 2a, 2b. However, it may also happen that both separator plates 2a, 2b have the tab 30, 31. For instance, two tabs 30, 32 are shown in FIG. 8, the tab 30 being part of the separator plate 2a and the tab 32 being part of the separator plate 2b. The tab 32 may have the same properties as the tab 30; however, the tabs 30, 32 may also have different features. For instance, each tab may be equipped with different functional elements such as codings 41, process monitoring areas 44, holding areas 43 and/or positioning openings 45. As illustrated in FIGS. 8 and 9, the tabs 30, 32 are arranged at different locations on the respective separator plates 2a, 2b. The tabs 30, 32 may be arranged such that the tabs 30, 32 partially overlap in a direction (z-direction) perpendicular to the plate plane of the bipolar plate 2. The tabs 30, 32 may optionally be welded together in a contact area, or otherwise connected to one another by a material bond. The welding sites 111 used for this may be provided for example in the respective process monitoring areas 44, so that the welding sites can later be examined with regard to quality or defects and thus make it possible to ascertain the quality or defects of the welding sites 110 of the plate body. Furthermore, in the case of a two-layer tab 39 separated from a bipolar plate, as shown in FIGS. 10 and 11 in the not yet separated state, it is possible to check, via a positioning element 45 in each of the layers, whether the plate bodies of the separator plates are also in the correct position with respect to one another, or were already in the correct position prior to being connected. If the edges of the positioning elements 45 of the two tabs 30, 32 are flush all the way round, the two separator plates 2a, 2b are positioned optimally with respect to one another, corresponding positioning elements 45 advantageously being provided in at least two pairs of tabs.

A method for producing the bipolar plate 2 is also proposed. The method comprises the steps:
providing a plate,
forming a first separator plate 2a having a plate body 21 and at least one tab 30, 31 formed in one piece with the plate body 21,
introducing a material weakening into the first separator plate 2a so as to form a predetermined breaking point 33, via which the tab 30, 31 can be separated from the plate body 21,
providing a second separator plate 2b,
forming the bipolar plate 2 by connecting the first separator plate 2a to the second separator plate 2b by a material bond.

The tab 30, 31 can then be separated from the first separator plate 2a along the predetermined breaking point. The separation may be carried out under the effect of heat, for example by means of laser radiation, a power surge or induction. Alternatively, the tab 30, 31 may be mechanically separated from the plate body 21, for example by cutting or tearing it off The second separator plate 2b may also have a corresponding tab 32. The bringing-together of the tabs 30, 32 and the material bonding of the partially overlapping tabs 30, 32 of the bipolar plate 2 of FIG. 8 is illustrated by the arrows in FIG. 9. Thereafter, the tabs 30, 32 can each be torn off from the bipolar plate 2 in the anticlockwise direction (see arrows). If the two tabs 30, 32 (or the tabs 31 and 32) are connected prior to being separated, they form a two-layer tab 39, as shown in FIGS. 10 and 11; the welded joint 111 is explicitly shown in said figures.

In the production process, the plate body 21 on the one hand and the process monitoring area 44 of the tab 30, 31, 32, 39 on the other hand may undergo the same processing steps, for example coatings, surface treatments and/or structurings, so that the subsequently separated tab 30, 31, 32, 39 can be used for example for quality control or quality assurance.

A method for testing a retention sample 30, 31, 32, 39 of the bipolar plate 2 is also proposed. First, the tab 30, 31, 32, which is still connected to the plate body 21, and the plate body 21 are each structured, surface-treated, inscribed, coated, embossed, punched and/or welded in an identical or at least similar manner. Thereafter, the retention sample 30, 31, 32, 39 is separated from the plate body 21. The method contains at least the step:

testing at least one material property or one processing parameter of the tab 30, 31, 32, 39.

The process monitoring area 44 of the tab 30, 31, 32, 39 is suitable for testing. Since the process monitoring area 44 has undergone the same processing steps as the plate body 21, properties of the bipolar plate 2 can be examined using the retention sample 30, 31, 32, 39, without the bipolar plate 2 itself having to be examined. In the example of FIG. 10, the applied sealing element 121, the conductivity coating 131, the weld seam 111 and the surface pre-treatment 141 are applied to or incorporated in the plate body 21 and the tab 30 of the upper separator plate 2a and the tab 32 of the lower separator plate 2b.

For example, destructive testing of the retention sample 30, 31, 32, 39 is possible, without the bipolar plate 2 itself having to be destroyed. Of course, non-destructive testing can also be carried out.

Features of the aforementioned methods can be combined with the features of the bipolar plates 2 and separator plates 2a, 2b, and vice versa.

The features, described above and shown in the figures, of the predetermined breaking point 33, the tab 30, 31 and/or the retention sample 30, 31 which are disclosed in connection with the two-layer bipolar plate 2 and the separator plates 2a, 2b can also be combined with a single-layer flow plate (not shown) in so far as they are compatible with use in a single-layer flow plate. The abovementioned retention sample 30, 31 and the abovementioned system can thus also be used with the flow plate. The flow plate may be configured for example as a unipolar plate, a bipolar plate, a humidifier plate and/or a separator plate and may be made for example of metal or plastic.

FIGS. 1-11 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

It will be appreciated that the configurations and routines disclosed herein are exemplary in nature, and that these specific embodiments are not to be considered in a limiting sense, because numerous variations are possible. Moreover, unless explicitly stated to the contrary, the terms "first," "second," "third," and the like are not intended to denote any order, position, quantity, or importance, but rather are used merely as labels to distinguish one element from another. The subject matter of the present disclosure includes all novel and non-obvious combinations and sub-combinations of the various systems and configurations, and other features, functions, and/or properties disclosed herein.

As used herein, the term "approximately" is construed to mean plus or minus five percent of the range unless otherwise specified.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

LIST OF REFERENCE SIGNS

1 electrochemical system
2 bipolar plate
2' bipolar plate
2a separator plate
2b separator plate
3 end plate
4 end plate
5 media port
6 stack
7 z-direction
8 x-direction
9 y-direction
10 membrane electrode assembly
11a-d through-openings
12 bead arrangement
12' bead arrangement
12a-d bead arrangement
13a-c passages
17 flow field
18 electrochemically active region
20 distribution and/or collection region
21 plate body
22 unstructured outer region
30 separable tab, optionally also retention sample
31 separable tab, optionally also retention sample
32 separable tab, optionally also retention sample
33 predetermined breaking point
34 indentation
35 perforation
36 stiffening structure
37 stiffening structure
38 stiffening structure
39 retention sample or separable two-layer tab 41 first coding
42 second coding
43 holding area
44 process monitoring area
45 positioning opening
110 weld seam (plate body)
111 weld seam (tab)
120 sealing element (plate body)
121 sealing element (tab)
130 conductivity coating (plate body)
131 conductivity coating (tab)
140 surface pre-treatment (plate body)
141 surface pre-treatment (tab)
t depth of the indentation
d thickness of the tab
b width of the predetermined breaking point

The invention claimed is:

1. A bipolar plate configured for an electrochemical system, comprising:
two separator plates which are connected to one another, at least one of the separator plates comprising:
a plate body; and
at least one tab which is formed in one piece with the plate body and separable from the plate body via a predetermined breaking point;
wherein the at least one tab has a first coding which is associated with the respective separator plate, and said separator plate has a second coding which corresponds to the first coding on the at least one tab.

2. The bipolar plate according to claim 1, comprising at least one through-opening for the passage of a fluid, and the at least one tab being arranged on an inner edge of the at least one through-opening or on an outer edge of the plate body.

3. The bipolar plate according to claim 1, wherein a stiffening structure, which extends at least partially along the predetermined breaking point, for separating the at least one tab in a defined manner along the predetermined breaking point is arranged on at least one side of the predetermined breaking point.

4. The bipolar plate according to claim 3, wherein the at least one tab has at least one further stiffening structure for stiffening the at least one tab.

5. The bipolar plate according to claim 4, wherein the at least one further stiffening structure is configured as an embossed structure, a bead, or a group of embossings.

6. The bipolar plate according to claim 1, wherein the predetermined breaking point comprises an indentation and/or a perforation.

7. The bipolar plate according to claim 1, wherein the respective coding comprises an inscription, a coloured pattern, a punched pattern and/or an embossed pattern.

8. The bipolar plate according to claim 1, wherein the at least one tab has at least one process monitoring area.

9. The bipolar plate according to claim 8, wherein the at least one process monitoring area has a coating, a surface treatment, and/or a structuring.

10. The bipolar plate according to claim 1, wherein the at least one tab has a positioning opening for receiving a centering pin or for position control.

11. The bipolar plate according to claim 1, wherein each of the two separator plates comprises one of the at least one tab, and the tabs at least partially overlapping in a direction perpendicular to a plate plane of the bipolar plate.

12. A retention sample of a bipolar plate for an electrochemical system, comprising:
a tab with a first breaking edge which can be separated from the bipolar plate via a predetermined breaking point, the tab having a process monitoring area and/or a first coding which is associated with the bipolar plate and/or with a separator plate of the bipolar plate.

13. A system, comprising the retention sample according to claim 12 and the associated bipolar plate for an electrochemical system, which comprises:
two separator plates which are connected to one another, the bipolar plate having a second breaking edge which has a shape complementary to the first breaking edge.

14. A method for producing a bipolar plate for an electrochemical system, comprising the steps of:
providing a plate;
forming a first separator plate having a plate body and at least one tab formed in one piece with the plate body;
introducing a material weakening into the first separator plate so as to form a predetermined breaking point, via which the tab can be separated from the plate body;
providing a second separator plate; and
forming the bipolar plate by connecting the first separator plate to the second separator plate;
wherein the at least one tab has a first coding which is associated with the first separator plate, and said first separator plate has a second coding on the plate body which corresponds to the first coding on the at least one tab.

15. The method according to claim 14, comprising the additional step of:
separating the tab from the first separator plate along the predetermined breaking point, by applying energy using laser or induction, or by separating the tab mechanically.

16. A bipolar plate configured for an electrochemical system, comprising:
two separator plates which are connected to one another, at least one separator plate of the two separator plates comprising:
a plate body; and
at least one tab which is formed in one piece with the plate body of the separator plate and is separable from the plate body via a predetermined breaking point;
wherein the at least one tab has a first coding which is associated with the bipolar plate, and the bipolar plate has a second coding which corresponds to the first coding on the at least one tab.

* * * * *